US008854029B2

(12) United States Patent
Mostov

(10) Patent No.: US 8,854,029 B2
(45) Date of Patent: *Oct. 7, 2014

(54) SYSTEM AND METHOD FOR SPACE CONTROL AND REMOTE MONITORING

(75) Inventor: Kirill Mostov, Berkeley, CA (US)

(73) Assignee: Radical Development Holding S.A., Lausanne, Vaud (CH)

( * ) Notice: Subject to any disclaimer, the term of this patent is extended or adjusted under 35 U.S.C. 154(b) by 216 days.

This patent is subject to a terminal disclaimer.

(21) Appl. No.: 13/346,351

(22) Filed: Jan. 9, 2012

(65) Prior Publication Data

US 2012/0105048 A1    May 3, 2012

Related U.S. Application Data

(63) Continuation of application No. 12/258,259, filed on Oct. 24, 2008, now Pat. No. 8,115,472.

(60) Provisional application No. 60/982,235, filed on Oct. 24, 2007.

(51) Int. Cl.
| G01R 23/16 | (2006.01) |
| G01S 13/00 | (2006.01) |
| G01S 13/88 | (2006.01) |
| G01S 7/02 | (2006.01) |
| G01S 7/41 | (2006.01) |
| G01S 13/34 | (2006.01) |
| G01S 13/42 | (2006.01) |

(52) U.S. Cl.
CPC ............... *G01S 13/888* (2013.01); *G01R 23/16* (2013.01); *G01S 7/024* (2013.01); *G01S 7/411* (2013.01); *G01S 7/415* (2013.01); *G01S 13/345* (2013.01); *G01S 13/42* (2013.01)
USPC ......................................... 324/76.21; 342/27

(58) Field of Classification Search
CPC ............ G01B 7/06; G01B 7/087; G01B 7/14; G01R 23/16; G06G 7/1921; G01F 23/284; G01S 13/04; G01S 13/56; F15B 15/2869
USPC ........ 324/76.21, 76.12, 76.11, 635, 644, 662, 324/671, 699, 716, 76.19; 342/27, 28, 107, 342/118, 128, 134, 137
See application file for complete search history.

(56) References Cited

U.S. PATENT DOCUMENTS

| 3,750,163 A | 7/1973 | Hecker |
| 3,922,673 A | 11/1975 | Bishop |

(Continued)

FOREIGN PATENT DOCUMENTS

WO    WO 2007/086916 A2    8/2007

OTHER PUBLICATIONS

PCT/US2008/081200—PCT Search Report and Written Opinion, Dec. 23, 2008, Kirsen Technologies Corporation.

(Continued)

*Primary Examiner* — Hoai-An D Nguyen
(74) *Attorney, Agent, or Firm* — Orrick, Herrington & Sutcliffe, LLP

(57) ABSTRACT

A system and method for space control and remote monitoring is disclosed. According to one embodiment, a frequency modulated signal is emitted from a radioscopic device having an antenna. The frequency of the reflected signal from a target is compared with the emitted frequency modulated signal to obtain a low-frequency signal. The low-frequency signal is processed to form signal pulsations spectrum using a fast Fourier transform. Each spectrum frequency represents a distance to the target.

19 Claims, 11 Drawing Sheets

(56) References Cited

U.S. PATENT DOCUMENTS

| | | | |
|---|---|---|---|
| 3,945,006 | A | 3/1976 | Cleeton |
| 3,949,397 | A | 4/1976 | Wagner et al. |
| 3,956,747 | A | 5/1976 | Leypold et al. |
| 4,155,087 | A | 5/1979 | Okrent |
| 4,320,298 | A | 3/1982 | Buford et al. |
| 4,323,898 | A | 4/1982 | Barnes et al. |
| 4,323,899 | A | 4/1982 | Barnes et al. |
| 4,566,009 | A | 1/1986 | Hanni et al. |
| 4,694,297 | A | 9/1987 | Sewards |
| 4,792,796 | A | 12/1988 | Bradshaw et al. |
| 4,821,291 | A | 4/1989 | Stevens et al. |
| 4,862,176 | A | 8/1989 | Voles |
| 4,879,756 | A | 11/1989 | Stevens et al. |
| 4,926,868 | A | 5/1990 | Larsen |
| 4,937,586 | A | 6/1990 | Stevens et al. |
| 5,124,709 | A | 6/1992 | Baron |
| 5,177,432 | A | 1/1993 | Waterhouse et al. |
| 5,245,534 | A | 9/1993 | Waterhouse et al. |
| 5,337,053 | A | 8/1994 | Dwyer |
| 5,374,815 | A | 12/1994 | Waterhouse et al. |
| 5,472,309 | A | 12/1995 | Bernard et al. |
| 5,504,487 | A | 4/1996 | Tucker |
| 5,507,291 | A | 4/1996 | Stirbl et al. |
| 5,532,465 | A | 7/1996 | Waterhouse et al. |
| 5,533,606 | A | 7/1996 | Yuyama |
| 5,561,431 | A | 10/1996 | Peele et al. |
| 5,612,700 | A | 3/1997 | Tucker |
| 5,646,616 | A | 7/1997 | Komatsu |
| 5,875,434 | A | 2/1999 | Matsuoka et al. |
| 5,877,962 | A | 3/1999 | Radcliffe |
| 5,943,841 | A | 8/1999 | Wunscher |
| 6,032,127 | A | 2/2000 | Schkolnick et al. |
| 6,121,920 | A | 9/2000 | Barrett |
| 6,161,038 | A * | 12/2000 | Schookin et al. .............. 600/519 |
| 6,208,908 | B1 | 3/2001 | Boyd et al. |
| 6,222,481 | B1 | 4/2001 | Abrahamson et al. |
| 6,308,109 | B1 | 10/2001 | Yuyama et al. |
| 6,337,654 | B1 | 1/2002 | Richardson et al. |
| 6,359,582 | B1 | 3/2002 | MacAleese et al. |
| 6,437,728 | B1 | 8/2002 | Richardson et al. |
| 6,505,093 | B1 | 1/2003 | Thatcher |
| 6,720,905 | B2 | 4/2004 | Levitan et al. |
| 6,765,527 | B2 | 7/2004 | Jablonski et al. |
| 6,856,272 | B2 | 2/2005 | Levitan et al. |
| 6,927,728 | B2 | 8/2005 | Vook et al. |
| 6,967,612 | B1 | 11/2005 | Gorman et al. |
| 6,972,714 | B1 | 12/2005 | Baharav et al. |
| 6,982,666 | B2 | 1/2006 | Temes et al. |
| 7,028,861 | B2 | 4/2006 | Sayers et al. |
| 7,046,186 | B2 | 5/2006 | Rosenberg et al. |
| 7,049,963 | B2 | 5/2006 | Waterhouse |
| 7,088,290 | B2 | 8/2006 | Ohno et al. |
| 7,196,654 | B2 | 3/2007 | Edwards et al. |
| 7,242,301 | B2 | 7/2007 | August et al. |
| 7,295,149 | B1 | 11/2007 | Wolf |
| 7,304,603 | B2 | 12/2007 | Reed et al. |
| 7,379,017 | B2 | 5/2008 | Dwelly et al. |
| 7,450,052 | B2 | 11/2008 | Hausner et al. |
| 7,626,505 | B2 | 12/2009 | August et al. |
| 7,878,965 | B2 | 2/2011 | Haber et al. |
| 7,920,088 | B2 | 4/2011 | Thompson et al. |
| 7,990,270 | B2 | 8/2011 | Mostov |
| 8,115,472 | B2 * | 2/2012 | Mostov .................... 324/76.21 |
| 2004/0053641 | A1 | 3/2004 | Leung et al. |
| 2004/0069849 | A1 | 4/2004 | Stevens et al. |
| 2004/0100379 | A1 | 5/2004 | Boman |
| 2004/0113783 | A1 | 6/2004 | Yagesh |
| 2004/0149822 | A1 | 8/2004 | Stevens et al. |
| 2004/0201454 | A1 | 10/2004 | Waterhouse |
| 2004/0205350 | A1 | 10/2004 | Waterhouse et al. |
| 2005/0029149 | A1 | 2/2005 | Leung |
| 2005/0029345 | A1 | 2/2005 | Waterhouse et al. |
| 2005/0043850 | A1 | 2/2005 | Stevens et al. |
| 2005/0083213 | A1 | 4/2005 | Stevens et al. |
| 2005/0086983 | A1 | 4/2005 | Stevens et al. |
| 2005/0104603 | A1 | 5/2005 | Peschmann et al. |
| 2005/0113703 | A1 | 5/2005 | Farringdon et al. |
| 2005/0149226 | A1 | 7/2005 | Stevens et al. |
| 2005/0156780 | A1 | 7/2005 | Bonthron et al. |
| 2005/0205817 | A1 | 9/2005 | Marcichow et al. |
| 2005/0251330 | A1 | 11/2005 | Waterhouse et al. |
| 2006/0124662 | A1 | 6/2006 | Reynolds et al. |
| 2006/0128023 | A1 | 6/2006 | Waterhouse et al. |
| 2006/0164232 | A1 | 7/2006 | Waterhouse |
| 2007/0194982 | A1 | 8/2007 | Stove |
| 2008/0211711 | A1 | 9/2008 | Mostov et al. |
| 2010/0027737 | A1 | 2/2010 | Mostov |

OTHER PUBLICATIONS

PCT/US2008/081200—Search Report, Aug. 2, 2011, Kirsen Technologies Corporation.
PCT/US2007/086664—Search Report and Written Opinion, Jul. 28, 2008, Kirsen Technologies Corporation.
PCT/US2008/084240—Search Report and Written Opinion, Feb. 4, 2009, Kirsen Technologies Corporation.
U.S. Appl. No. 12/258,259; Notice of Allowance mailed Oct. 7, 2011.
U.S. Appl. No. 11/951,915; Office Action mailed Feb. 26, 2009.
U.S. Appl. No. 11/951,915; Office Action mailed Dec. 7, 2009.
U.S. Appl. No. 11/343,560; Office Action mailed Jan. 18, 2008.
U.S. Appl. No. 11/343,560; Office Action mailed Sep. 11, 2008.
U.S. Appl. No. 11/343,560; Notice of Allowance mailed Feb. 2, 2009.

* cited by examiner

SYSTEM AND METHOD FOR SPACE CONTROL AND REMOTE MONITORING

The present application is a continuation of U.S. patent application Ser. No. 12/258,259 titled "A System and Method for Space Control and Remote Monitoring" filed on Oct. 24, 2008 now U.S. Pat. No. 8,115,472, which claims the benefit of and priority to U.S. Provisional Patent. Application No. 60/982,235 filed on Oct. 24, 2007, and both are hereby incorporated by reference in their entirety for all purposes.

FIELD

The field of the invention relates generally to object monitoring and detection systems and more particularly relates to devices for remotely detecting and monitoring concealed objects.

BACKGROUND

One of the major problems associated with providing safety is the control of a limited space in order to detect movements of people having hostile intentions with weapons or explosive devices. Safety has become more and more important, and there is an increasing need for a device that could fully control limited space.

Previous detection methods are based on video cameras and sensors such as thermal sensors and metal detectors. Video cameras only detect targets within a certain range, and sensors can only provide limited information about the detected target. Conventional imaging and sensor systems cannot detect targets that are hidden behind walls. Those systems are stationary, thus have to be installed in preliminarily selected places. Systems that use cameras may not be secretly installed; thus, they are much less effective than concealed ones.

Automatic detection of concealed bombs and weapons has become more and more important. Most known systems for detecting the presence of explosive devices and weapons are electromagnetic-based and require a subject to pass through a fixed passageway. When metallic objects pass through the passageway, a warning signal is activated if a change in the magnetic flux is detected. Electromagnetic-based systems either detect or fail to detect a metal object; thus they make no determination relative to the amount of metal present. Non-threat objects such as keys, jewelry, watches, and metal-framed eyeglasses may trigger a false alarm.

The above-described devices and systems can register weapons and explosive devices, but they do not detect the emotional state of the person who is carrying suspicious objects, which is very important in automated systems. Emotional state recognition is based on the heart and breathing data of a subject.

SUMMARY

A system and method for space control and remote monitoring is disclosed. According to one embodiment, a frequency modulated signal is emitted from a radioscopic device having an antenna. The frequency of the reflected signal from a target is compared with the emitted frequency modulated signal to obtain a low-frequency signal. The low-frequency signal is processed to form signal pulsations spectrum using a fast Fourier transform. Each spectrum frequency represents a distance to the target.

The above and other preferred features, including various novel details of implementation and combination of elements will now be more particularly described with reference to the accompanying drawings and pointed out in the claims. It will be understood that the particular methods and apparatus are shown by way of illustration only and not as limitations. As will be understood by those skilled in the art, the principles and features explained herein may be employed in various and numerous embodiments.

BRIEF DESCRIPTION OF THE DRAWINGS

The accompanying drawings, which are included as part of the present specification, illustrate the presently preferred embodiment of the present invention and together with the general description given above and the detailed description of the preferred embodiment given below serve to explain and teach the principles of the present invention.

Figure 1:
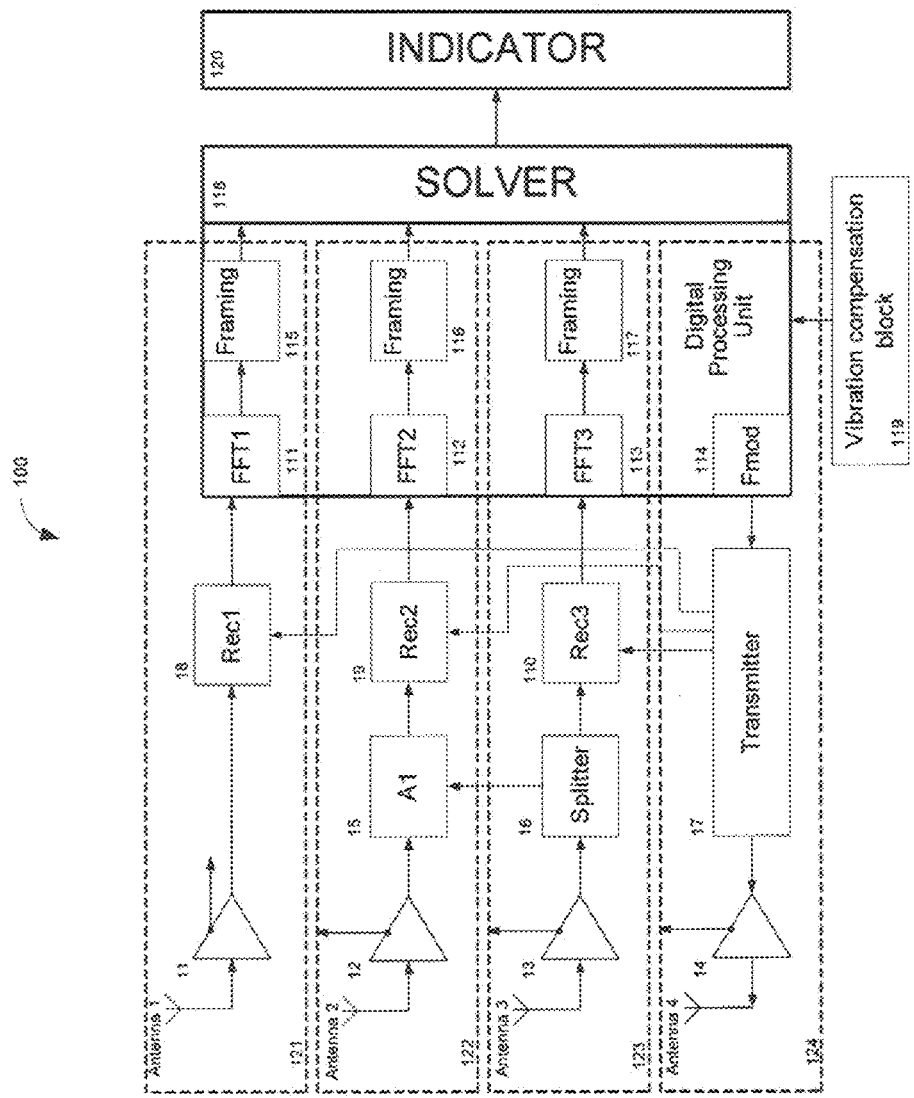
FIG. 1 illustrates a block diagram of an exemplary radioscopic device (RSD), according to one embodiment.

It should be noted that the figures are not necessarily drawn to scale and that elements of similar structures or functions are generally represented by like reference numerals for illustrative purposes throughout the figures. It also should be noted that the figures are only intended to facilitate the description of the various embodiments described herein. The figures do not describe every aspect of the teachings described herein and do not limit the scope of the claims.

DETAILED DESCRIPTION

A system and method for space control and remote monitoring is disclosed. The present system and method detects and identifies suspicious objects hidden under clothes or in luggage. The device also presents a high-resolution radio image of targets of interest for manual analysis. The present system and method measures physiological parameters and psycho-physiological information of a target subject by remote detection of a hostile intent.

In the following description, for the purposes of explanation, specific nomenclature is set forth to facilitate an understanding of the various inventive concepts disclosed herein. However, it will be apparent to one skilled in the art that these specific details are not required in order to practice the various inventive concepts disclosed herein.

The present system and method also relates to apparatus for performing the operations herein. This apparatus may be specially constructed for the required purposes, or it may comprise a general-purpose computer selectively activated or reconfigured by a computer program stored in the computer. Such a computer program may be stored in a computer-readable storage medium, such as, but is not limited to, any type of disk including floppy disks, optical disks, CD-ROMs, and magnetic-optical disks, read-only memories, random access memories, EPROMs, EEPROMs, magnetic or optical cards, or any type of media suitable for storing electronic instructions, and each coupled to a computer system bus.

The methods presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

According to one embodiment, the present system detects the presence of moving and motionless, but breathing people, even behind obstacles, the presence of explosive device s and weapons, the presence of people with hostile intend, and remotely determines physical parameters and emotional state of the traced person or patient. For example, objects of a larger size such as a suicide belt with metal parts may be detected at distances of up to 50 meters. According to one embodiment, the present system is used as a hand held device, allowing to use under field conditions.

The present system detects a subject, motionless or moving, or behind obstacles, effectively detects weapons and bombs that the subject carries, and determines the azimuth and distance to a threatening target. Also the present system remotely detects psycho-physiological information of a traced subject with a hostile intent. According to one embodiment, the present system may be used in a hospital as a remote cardiac monitor or as a multifunctional device for measuring physiological parameters such as heart rate, breath rate, vasomotorial functions, muscle tone, oxygen saturation, and sweating. The present system is mobile without requiring installation, thus can be easily used under field conditions or in transport.

FIG. 1 illustrates a block diagram of an exemplary radioscopic device (RSD), according to one embodiment. RSD 100 includes three channel receiving channels 121-123, transmitting channel 124, solver 118, and indicator 120. Different numbers of receivers and transmitters may be used without deviating from the scope of the present subject matter. Transmitting channel 124 includes frequency modulator 114, transmitter 17, and antenna 14 with vertical polarization. Probing signals are modulated by frequency modulator 114 and transmitted to transmitter 17. The modulated probing signals from transmitter 17 are transmitted via antenna 14. Channel 122 has antenna 12 with vertical polarization, difference diagram 15, microwave frequency receiver 19, fast Fourier transformation (FFT) block 112, and framing block 116. Channel 123 has antenna 13 with vertical polarization, splitter 16, microwave frequency receiver 110, FFT block 113, and framing block 117. Channels 122 and 123 are used for azimuth determination. Channel 123 is also responsible for distance determination. According to one embodiment, channel 122 is required to determine azimuth to the target. If channel 122 is not enabled, splitter 16 in channel 123 is not necessary. Channel 121 has antenna 11 with horizontal polarization, microwave frequency receiver 18, FFT block 111, and framing block 115. Channel 121 is required to detect weapons. If channel 121 is not enabled, polarization of antennas 12 and 13 is not necessary. Although FFT blocks 111-113 are shown in the present example, it is appreciated that other frequency-based transformation may be used without deviating the scope of the present subject matter.

Figure 2:
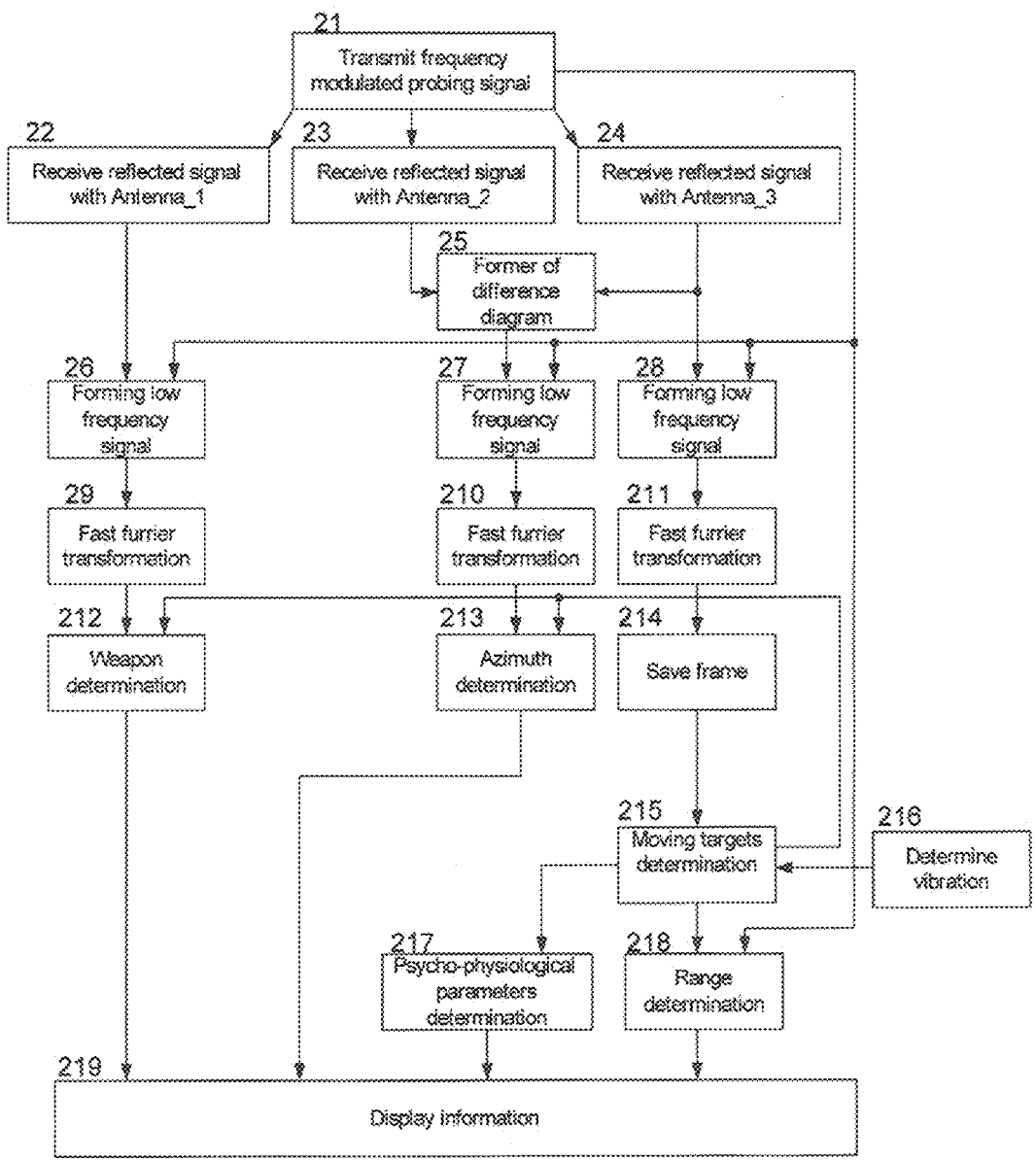
FIG. 2 illustrates a flow chart of an exemplary RSD, according to one embodiment.
Figure 3:
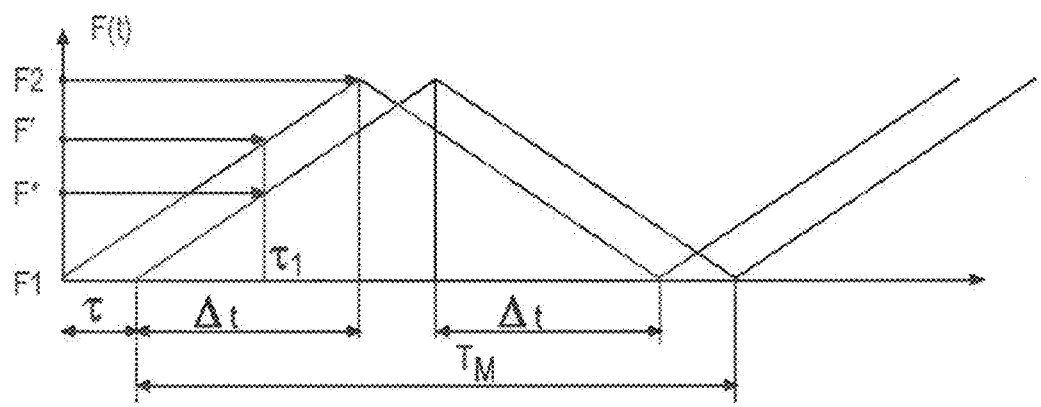
FIG. 3 illustrates an exemplary process for determining the distance to a target, according to one embodiment.

FIG. 2 illustrates a flow chart of an exemplary RSD, according to one embodiment. FIG. 3 illustrates an exemplary process for determining the distance to a target, according to one embodiment. Referring to FIG. 1, antenna 14 of RSD 100 with vertical polarization starts radiating linear modulated signal F' that was received from transmitter 17. The central frequency of the reflected signal received by receiving antennae 11-13 is correlated with the best cinderblock penetration at a minimal size of RSD 100. In one embodiment, the central frequency of 2.4 GHz is used for best cinderblock penetration, but it is appreciated that other frequencies may be used without deviating the scope of the present system and method. Receiving antennae 11, 12, and 13 receive the reflected signal. The central frequency of the emitted signal, for a given the size of RSD 100, is selected to monitor targets through walls of various types, thicknesses, and materials.

Figure 4:
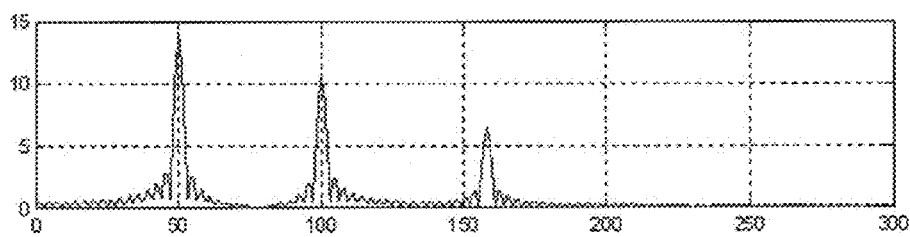
FIG. 4 illustrates an exemplary signal reflected from multiple objects, according to one embodiment.

According to one embodiment, RSD 100 detects breathing live targets that are moving or motionless, such as a human or an animal. Live targets are detected based on the signal from antenna 13. The received signal F* from antenna 13 is subtracted with the transmitting signal F', and the resulting low frequency signal is sent to FFT module 113. The result of FFT is saved in framing block 117. In the next step, a new frame is saved, and the neighbor frames are subtracted as illustrated in FIG. 4. Peaks on the resulting spectrum are correlated with moving targets.

FIG. 4 illustrates an exemplary signal reflected from multiple objects, according to one embodiment. When a target is found with distance information, azimuth and biological parameters of the detected target are obtained.

When RSD 100 is used in a "free hand," it experiences fluctuations, which generates a false movement of the target. In order to eliminate (or indemnify) of false movements, vibration compensation block (VCB) 119 is used. VCB 119 detects the fluctuation of RSD 100 and sends the data to solver 118 for signal compensation.

According to one embodiment, VCB 119 contains an accelerometer and a magnetic sensor. Accelerometer is used to determine the frequency spectrum of "linear fluctuation" of RSD 100. Angular turns of RSD 100, however, change the vector of gravitation. Therefore, the magnetic sensor is used to determine the angular turn indicated by parasitic components of the vector of gravitation. The calculated parasitic components of the vector of gravitation are used to compensate the signal obtained by the accelerometer.

According to one embodiment, the distance to a live target is calculated as illustrated in FIG. 3. RSD transmitter 17 radiates microwave signal F' with the frequency sweeping from F1 to F2 within time period $T_M$. The emitted signal from the target at distance R is received by receiving antennae 11-13. The emitted signal has frequency F with a time delay, $\tau=2*R/c$, where c is the speed of light in air. Frequency $F_B$, the difference of frequency F' and F* during time $\tau 1$, is determined by the following equations:

$$F' = F_1 + \frac{2(F_2 - F_1)}{T_M}\tau_1,$$

-continued $$F^* = F_1 + \frac{2(F_2 - F_1)}{T_M}(\tau_1 - \tau),$$

$$F_B(R) = F' - F^* = \frac{4(F_2 - F_1)R}{cT_M}.$$

Therefore, distance R is calculated by $$R = \frac{cT_M(F' - F^*)}{4(F_2 - F_1)}.$$

Figure 5:
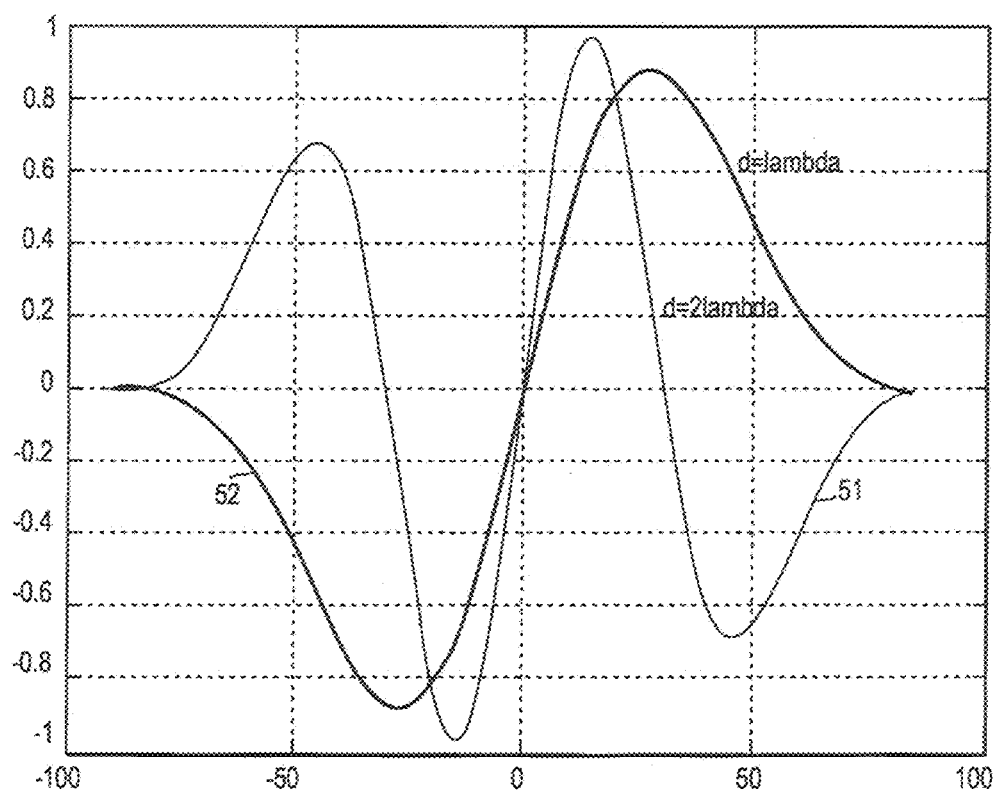
FIG. 5 illustrates an exemplary orientation diagram of channel 122 for determining the azimuth of a detected target, according to one embodiment.

FIG. 5 illustrates an exemplary orientation diagram of channel 122 for determining the azimuth of a detected target, according to one embodiment. RSD 100 determines the azimuth of the target after calculating the distance R to the target. Framing block 116 analyzes the amplitude of the frequencies at which the targets were detected. D is the distance between antenna 12 and 13 and, lambda is the wave length. Axis x is the degree from normal line of antenna 13.

Within ±30° sector value of the signal is proportional to the azimuth of the target. When the distance between the antennas becomes smaller, the spectrum width increases while the slope of the curve decreases.

The azimuth of the target is determined based on the turnstile characteristic $$P = \frac{A_j}{A_k},$$

where $A_j$ and $A_k$ are the magnitudes of signals at frequencies calculated from channels 122 and 123. P defines the azimuth sign and does not depend on the distance R or the effective radar cross section. On linear part of the orientation diagram FIG. 5 azimuth $\phi$ is determined by $\phi = S \cdot P$, where S is the slope of curve of the turnstile characteristic P.

The above-described method for calculating the azimuth of the target is simple, but is limited to the cases when the distance to the target is significantly bigger than distance between the antennas.

According to one embodiment, there is another more precise method of azimuth determination. High accuracy of distance measurement (r.m.s. error 1 cm) allows determining azimuth with desirable accuracy when distance between antennae is about 20 cm. Separation is limited by the device dimensions.

Figure 6:
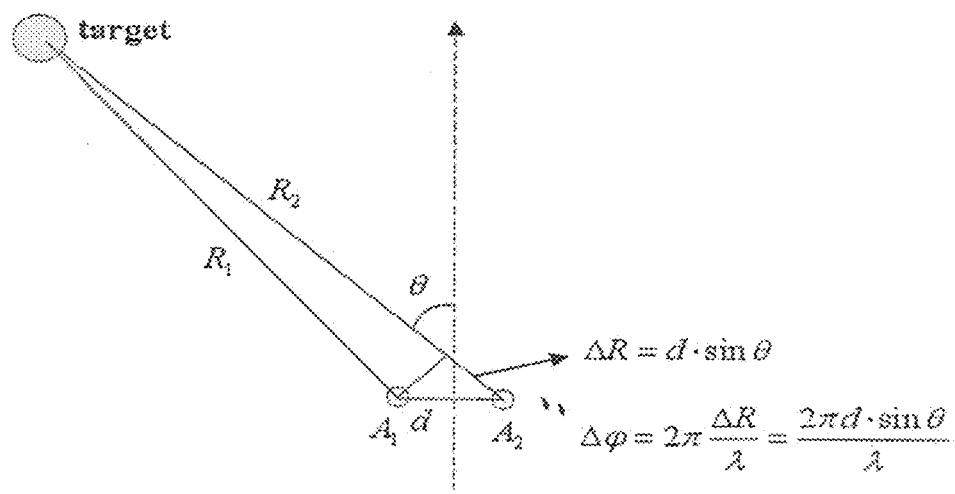
FIG. 6 illustrates a triangulation method for calculating the azimuth $\theta$ to a target, according to one embodiment.

FIG. 6 illustrates a triangulation method for calculating the azimuth θ to a target, according to one embodiment. The difference of the distance to the target, ΔR, from antenna 11 and antenna 12 causes the phase of the received signals exhibit a delay by:

$$\Delta \varphi = \frac{\Delta R}{\lambda} 2\pi = \frac{L \cdot \sin\theta}{\lambda} 2\pi = k \cdot L \cdot \sin\theta,$$

where $$k = \frac{2\pi}{\lambda},$$

λ is the wave length of the received signal.

The azimuth θ is calculated with known values of Δφ and λ.

Figure 7:
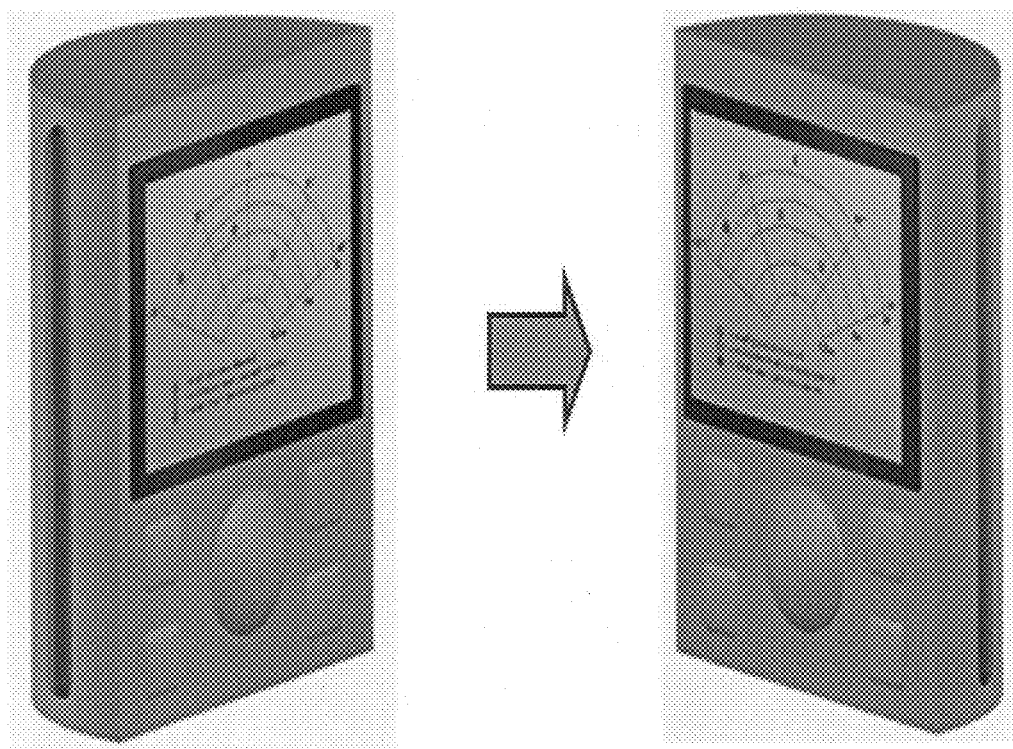
FIGS. 7-9 illustrate variants of RSD 100 with a special feature for manual scanning, according to one embodiment.
Figure 8:
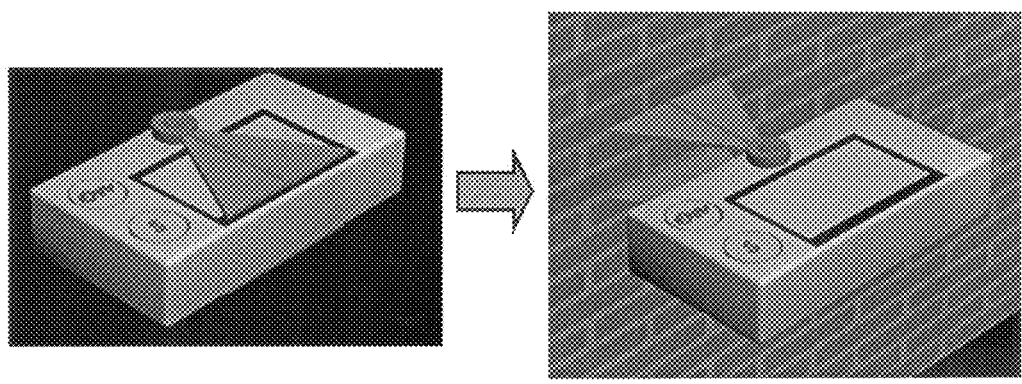
Figure 9:
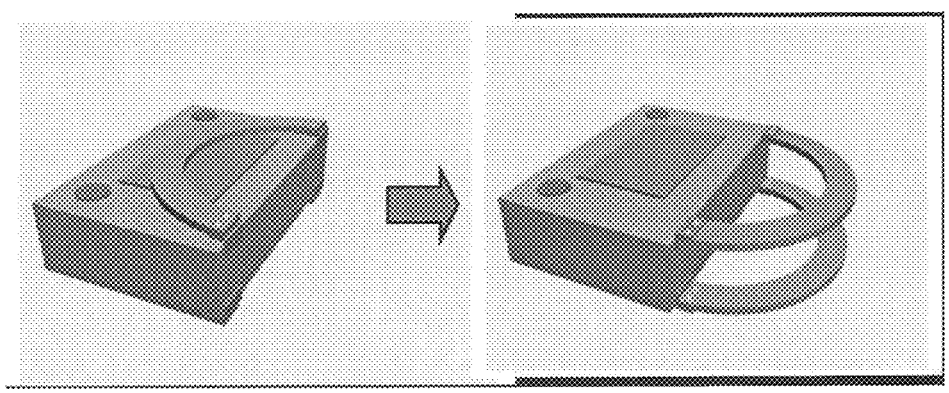

FIGS. 7-9 illustrate variants of RSD 100 with a special feature for manual scanning, according to one embodiment. Manual scanning is accomplished by rotating RSD 100 while pressing it against a spatial reference such as a wall.

According to one embodiment, a magneto-resistive magnetic sensor is used for rotation angle measurement. Magnetic sensors measure two basic components: earth magnetic field M independent of the device position and the parasitic magnetic field of the ambient environment rigidly linked with the orientation of RSD 100, $M_X^0$, $M_Y^0$, $M_Z^0$.

The orientation of RSD 100 with respect to vector $M = M_X^0$, $M_Y^0$, $M_Z^0$ is determined based on the implementation of the following procedures. Initial calibration is performed to determine the components of vector M. The components of vector M may be fine tuned before the scan or when RSD 100 is turned on. In order to account for the parasitic components of vector M, the angular parameter a with respect to the earth magnetic vector is defined.

According to one embodiment, RSD 100 detects weapons. The presence of weapons is based on a depolarized analysis of the signal reflected from a target. The depolarized signal received by antennae 11-13 of RSD 100 with horizontal and vertical polarization is analyzed to determine the carriage of concealed weapons and shrapnel.

The reflected signal reflected from a target has two major components: a diffusive background and bright dots. The background may appear diffused because of the target's surface roughness. The contribution of bright dots is greater than that of the diffusive background signal within the reflected depolarized signal. Maximum depolarization occurs when the size of the observed small elements is half of the wavelength of the probing signal. Small elements may be the shrapnel in a suicide belt, or bolts, ball-bearings, nuts, nails, fragments of metallic pieces. For example, if the frequency of 50 GHz is used, the wavelength is about 6 mm. Small elements of the size of 3 mm exhibit a maximum depolarization effect.

Polarization of the background may be random and weak depending on the polarization of the probing signal. The diffusive background contributes to the reflected signal. In contrast, bright dots of a target make a significant contribution to the diffused signal because the target may have small mirrors normally focused to a line of sight. If the size of these mirrors is half of the wavelength (i.e., half wave dipole), the contribution to the diffused signal is maximal. Because the bright dots of the target are noticeable because of their comparatively larger reflectivity to other dots of the background, a small mirror effect is observed. The presence of these small minors (bright spots) allows for the identification of typical threats by their relative position with respect to each other and the background. The turn of the polarization plane of the diffused radiation depends on the orientation of the dipole. If probing radiation is polarized either vertically or horizontally, and the dipole is focused under 45°, the diffused signal contains both vertical and horizontal polarization. The cross-polarization is evaluated by the polarization coefficient:

$$B = \frac{A_k - A_i}{A_k + A_i}$$

where $A_i$ and $A_k$ are the amplitudes of the received signals with horizontal and vertical polarization.

If the target is a half-wave dipole rotated by 45° to the horizon, the depolarization coefficient B is zero. Since actual targets have randomly oriented dipoles, the polarization factor ranges between 0 and 1. The lower the polarization factor, the greater the probability that a weapon or an explosive belt exists.

Small pieces of firearms and steel at a certain perspective also exhibit depolarization. As the weapon has fewer small pieces than an explosive belt, the coefficient of depolarization significantly differs due to the difference in the amount of small pieces expressed by the relationship:

$$B_{weapon} > B_{explosive\_belt}.$$

Since RSD 100 detects moving and living subject, the detection of weapons and explosive belts may be done selectively for each irradiated person. This allows for armed persons to be isolated and displayed on the screen.

Figure 10:
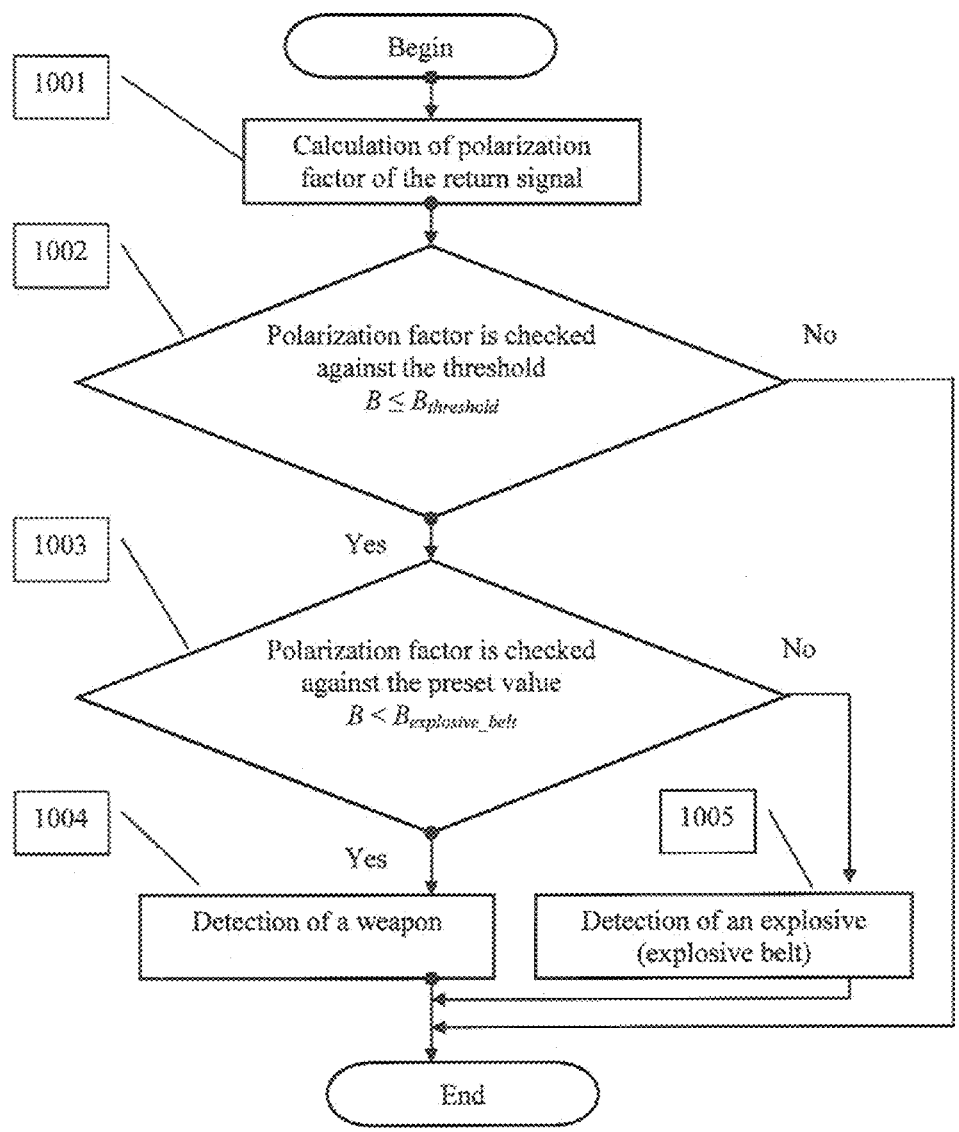
FIG. 10 illustrates a flow chart of an exemplary weapon detection process, according to one embodiment.

FIG. 10 illustrates a flow chart of an exemplary weapon detection process, according to one embodiment. The polarization factor of a return signal is calculated (1001). The polarization factor B is checked (1002) against threshold $B_{threshold}$. In one embodiment, $B_{threshold}$ may be determined experimentally. If $B \leq B_{threshold}$, the polarization factor B of the signal being analyzed is checked (1003) against the preset value $B_{explosive\_belt}$. If $B_{threshold} > B > B_{explosive\_belt}$, a decision is made (1004) that the target carries firearms or cold arms. If $B < B_{explosive\_belt}$, a decision is made (1005) that the target carries an explosive belt.

Figure 11B:
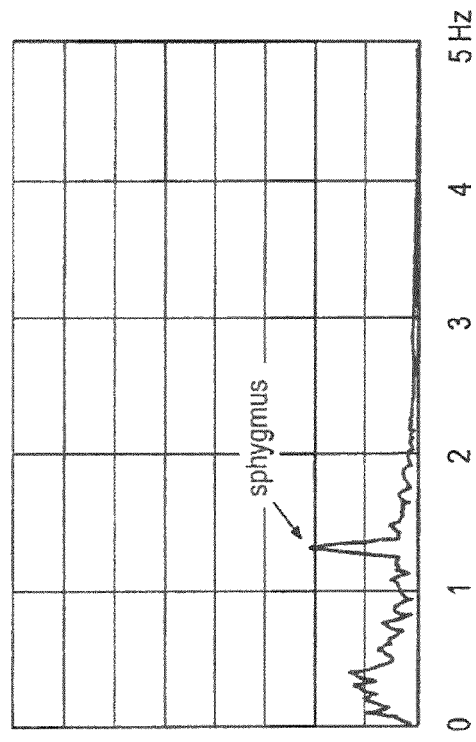
FIG. 11 illustrates an exemplary scanned signal containing heart and respiration rate information, according to one embodiment.
Figure 11A:
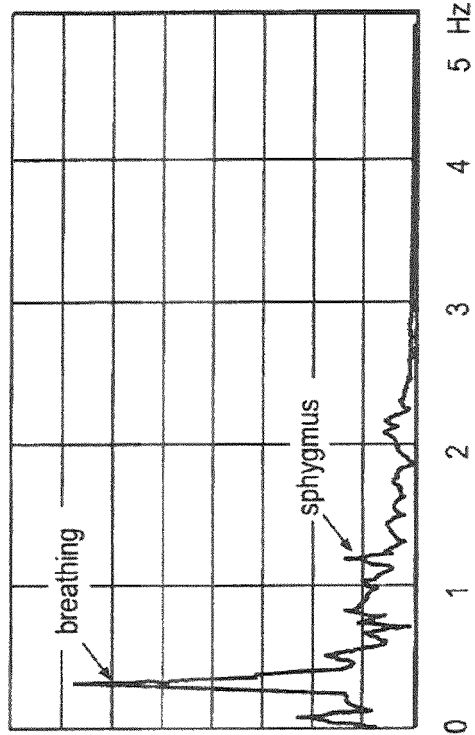

According to one embodiment, RSD 100 determines psycho-physiological parameters of a scanned subject. Slow fluctuations of the probing signal allow for remote measurement of different rhythms of the scanned subject. The probing signal may be received through an opaque barrier. In one embodiment, the psycho-physiological parameters may be scanned for the entire group of people within the range of measurement, and a person with anomalic psycho-physiological parameter is detected. The scanning process may be carried out over several seconds. FFT is performed on a series of scanned signals, and signal pulsations spectrum for each target is formed. FIG. 11 illustrates an exemplary scanned signal containing heart and respiration rate information, according to one embodiment.

Figure 12:
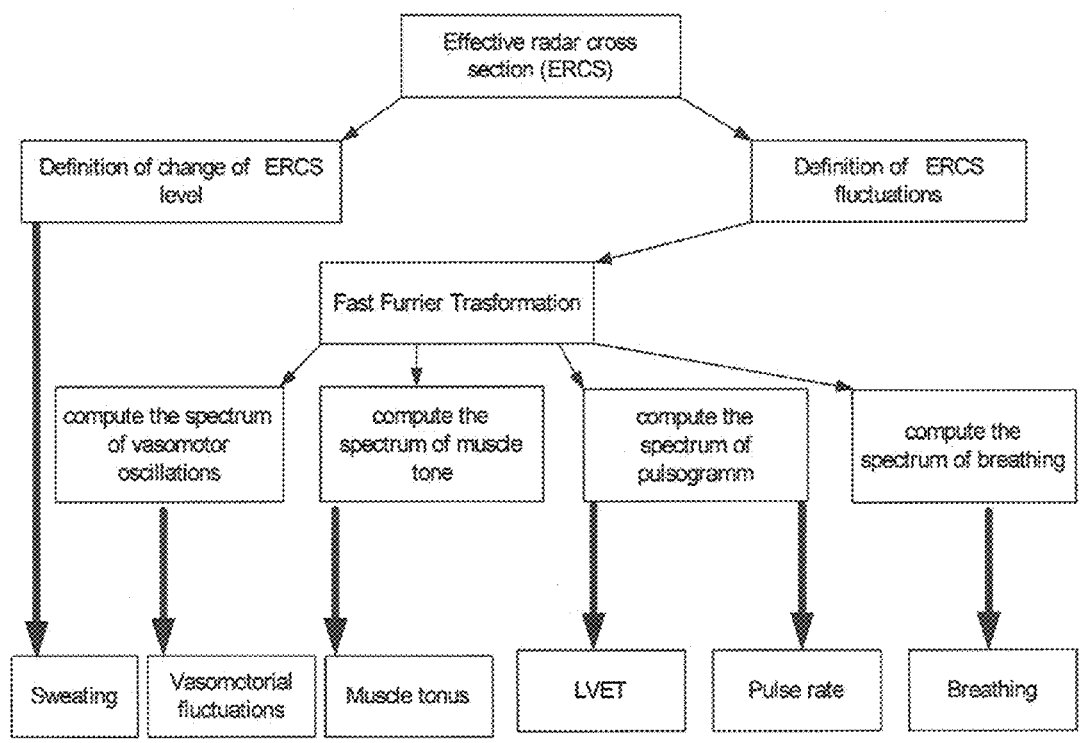
FIG. 12 illustrates a flow chart of an exemplary process to determine psycho-physiological parameters, according to one embodiment.

FIG. 12 illustrates a flow chart of an exemplary process to determine psycho-physiological parameters, according to one embodiment. An analysis of the changes in effective radar cross section (ERCS) reveals the changes in perspiration of the scanned subject. Fluctuations in ERCS also give information about plethysmogram, breathing, vasomotorial functions, and muscle tonus of the scanned subject. Each physiological parameter has its own fluctuation frequency. For example, typical vasomotorial signals range between 0.0017-0.017 Hz, muscle tonus signals between 0.017-0.17 Hz, breathing signals between 0.08-0.5 Hz, and heart beat signals between 0.67-4 Hz.

Figure 13:
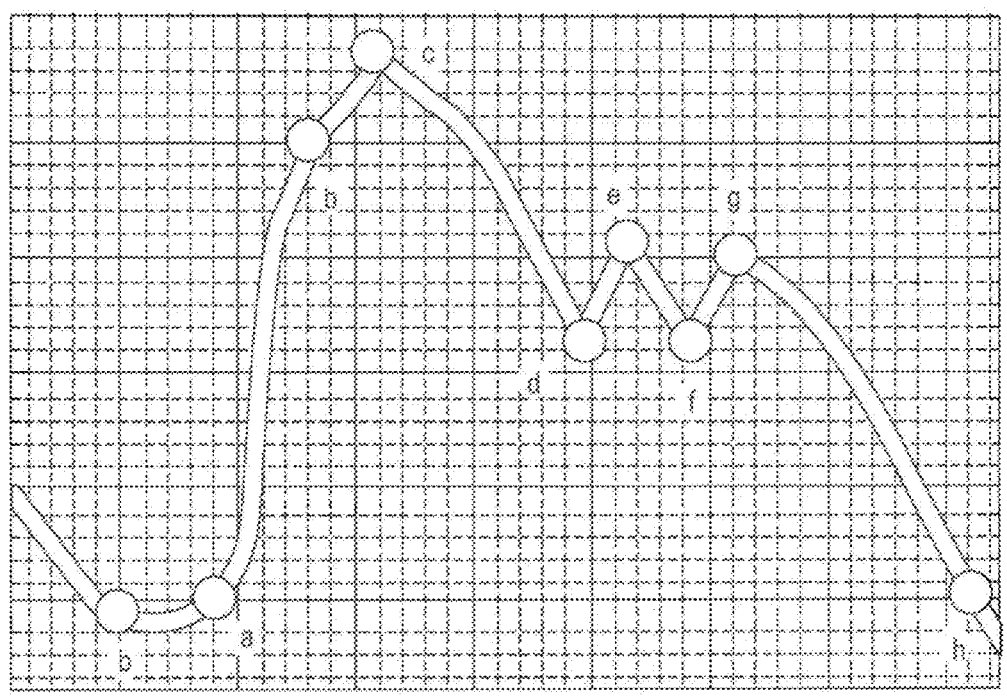
FIG. 13 illustrates an exemplary waveform describing heart-muscle operation, according to one embodiment.

FIG. 13 illustrates an exemplary waveform describing heart-muscle operation, according to one embodiment. From the waveform constructed by RSD 100, left ventricular ejection time (LVET) and heart beat may be determined. LVET is the heart parameter (speed of contraction of the left ventricle), which is known to be correlated with a "hostile intent." The left ventricle pumps blood on the large circuit, and the right ventricle pumps blood on the smaller respiratory/lung circuit.

According to one embodiment, RSD 100 detects plethysmogram in real-time. A plethysmogram is a derived measurement of heart activity. A plethysmogram may be used to evaluate the heart activity and compute LVET based on an analysis of the fluctuations in the amplitude of the reflected signal and the relative position of the characteristic points on the plethysmogram.

In FIG. 13, a typical heart cycle (plethysmogram) having the following phases of interest is shown; a-b-c is a systole phase with an increased pressure during heart muscle contraction; c-d is the phase of reduction of pressure at the tail end of systole; e is the phase of closing half moon valves; and f-g-h is the phase of reduction of blood pressure during diastole.

Phase a-b-c, the isometric contraction of the ventricle's systole, occurs with closed heart valves. The beginning of this phase coincides with the phase of abrupt increase in the internal to ventricles pressure. The derivative at point a may be used for the analysis of intensity and speed of ventricle operation. The amplitude of a-b-c correlates to the arterial pressure; one of the main parameters of heart operation. The measured peripheral blood pressure is analyzed as low-pass-filtered arterial pressure.

The operation of left ventricle is characterized by (a) the heartbeat frequency; (b) the speed, with which the left ventricle muscle tissue is changing its tone, e.g., transitions from the relaxed to the contracted state; and (c) the blood pressure created by the left ventricle for opening the valve (instantaneous power of the pump with respect to one blood ejection from the ventricle).

Since the right ventricle operates at an order of magnitude lower power, the plethysmogram of the peripheral pulse provides rich source of information on the physiology of the left ventricle. By analyzing physiological parameters, a hostile intent of the scanned subject is determined.

According to one embodiment, the psychological condition of a live subject is characterized by the values of physiological parameters as illustrated in FIG. 11. Depending on the psychological condition, for example stress levels, a person may experience sweating, changes in breathing rate and heart rate, changes in muscle tone, etc. These changes are mainly correlated with various hemodynamic changes (e.g., changes in the amount/volume/presence of blood in various human organs, vessels and muscles). Hemodynamic changes may be measured by observing the changes in total ERCS of the observed person or ERCS of each body part separately. The signals pertaining to these psychological parameters are compared with critical and baseline thresholds that are determined experimentally. Relative changes of observable physiological parameters are taken into account and analyzed in light of predetermined templates or rules. In one embodiment, a comparison is made between the observed values with a library of values defining typical various psychological conditions. The differences between the observed values and the values from the library determine the psychological condition of the observed person, and a subsequent conclusion is made about the possible hostile intent of the observed person.

A system and method for space control and remote monitoring have been described. It is understood that the embodiments described herein are for the purpose of elucidation and should not be considered limiting the subject matter of the present patent. Various modifications, uses, substitutions, combinations, improvements, methods of productions without departing from the scope or spirit of the present invention would be evident to a person skilled in the art.

I claim:

1. A system, comprising:
a radioscopic device for remote detection, the radioscopic device comprising:
a transmitting antenna;
a receiving antenna;
a high frequency signal processing module;
digital signal processing module; and
display and a power supply; and instructions executable by the radioscopic device, the instructions for configuring the radioscopic device to perform emitting a frequency modulated signal;

scanning a plurality of targets simultaneously within a measurement range of the radioscopic device;

receiving a reflected signal from a target of the plurality of targets;

subtracting the frequency modulated signal with the reflected signal for obtaining a low-frequency signal;

processing the low-frequency signal using fast Fourier transform (FFT);

forming signal pulsations spectrum based on the results of the FFT, wherein each spectrum frequency represents a distance to the target;

determining the distance to the target;

determining psycho-physiological parameters of the target, wherein determining psycho-physiological parameters of the target comprises analyzing a change in the effective radar cross section and calculating left ventricular ejection time (LVET) of the target;

identifying the target as an anomalic target of the plurality of targets based on the psycho-physiological parameters; and determining a hostile intent of the target based on the psycho-physiological parameters.

2. The system of claim 1, wherein the radioscopic device is configured to further perform monitoring the low-frequency signal at a time interval;

saving the low-frequency signal in a memory;

updating the distance to the target; and determining whether the target is moving.

3. The system claim 1, wherein determining the psycho-physiological parameters of the target comprises further comprising:

analyzing the low-frequency signal of the target; and detecting the presence of heart beat and breath wave.

4. The system of claim 3, wherein the radioscopic device is configured to further perform determining whether the target is a live subject.

5. The system of claim 3, wherein the radioscopic device is configured to further perform receiving the reflected signal with at least two antennae;

analyzing the amplitude of the low-frequency signal; and determining an azimuth of the target based on a ratio of the amplitudes of the reflected signal at the two antennae.

6. The system of claim 3, wherein the radioscopic device is configured to further perform scanning the radioscopic device with a narrow diagram of orientation of the antenna; and determining an azimuth of the target, wherein the azimuth is equal to the rotation angle of the radioscopic device.

7. The system of claim 6, wherein the scanning is realized through manual turn of the radioscopic device.

8. The system of claim 3, wherein the radioscopic device is configured to further perform receiving the reflected signal with at least two antennae with orthogonal polarization;

calculating depolarization coefficient using the reflected signal;

analyzing the depolarization coefficient of the reflected signal; and detecting a weapon based on the depolarization coefficient, wherein the weapon is detected if the depolarization coefficient is lower than a threshold value.

9. The system of claim 8, wherein only live subjects are analyzed for weapon detection.

10. The system of claim 4, wherein the radioscopic device is configured to further perform analyzing an increase in the intensity of the reflected signal from the skin surface of the live subject; and calculating perspiration from the live subject.

11. The system of claim 1, wherein the transmitting antenna has a narrow diagram of orientation and a manual scanning module for determining an azimuth of a target.

12. The system of claim 4, wherein determining psycho-physiological parameters of the target further comprises:

analyzing changes in the effective radar cross section using the amplitudes of the reflected signal; and determining arterial blood pressure of the live subject.

13. The system of claim 4, wherein determining psycho-physiological parameters of the target further comprises:

analyzing fluctuations of amplitudes of the received signal caused by changes in the effective radar cross section; and calculating muscle tone of the live subject.

14. The system of claim 4, wherein the radioscopic device is configured to further perform determining a hostile intent of the live subject is based on one of analyzed signals of LVET, perspiration, heart rate, blood pressure, vasomotor fluctuations data, muscle tone and rush of blood to the organs.

15. The system of claim 1, wherein the radioscopic device has at least two receiving antennae to determine an azimuth of a target based on a triangular method where distance to the target from each antenna is calculated using wave phase.

16. The system of claim 15, wherein the two receiving antennae have orthogonal polarization to calculate depolarization of the target.

17. The system of claim 1, wherein the radioscopic device has at least three receiving antennae, two of the three receiving antennae have orthogonal polarization.

18. The system of claim 1 wherein the radioscopic device further comprises a module for compensating vibration.

19. The system of claim 18, wherein the module comprises an accelerometer and/or a magnetic sensor.

\* \* \* \* \*